United States Patent [19]

Rubin et al.

[11] Patent Number: 4,670,388
[45] Date of Patent: Jun. 2, 1987

[54] METHOD OF INCORPORATING DNA INTO GENOME OF DROSOPHILA

[75] Inventors: Gerald M. Rubin; Allan C. Spradling, both of Baltimore, Md.

[73] Assignee: Carnegie Institution of Washington, Washington, D.C.

[21] Appl. No.: 454,518

[22] Filed: Dec. 30, 1982

[51] Int. Cl.[4] .................. C12N 15/00; C12N 1/00
[52] U.S. Cl. .................. 435/172.3; 435/317; 935/24; 935/53; 935/63; 935/70
[58] Field of Search .............. 435/172, 172.3; 935/24, 935/52, 53, 54, 62, 63, 64; 119/1

[56] References Cited

PUBLICATIONS

Germeraad, Nature vol 262 pp. 229-231 Jul. 15, 1976.
Flavell et al., Nature vol. 292 pp. 591-595 Aug. 13, 1981.
Starlinger, Genetic Engineering to Biotechnology-The Critical Transition, John Wiley & Sons Ltd. pp. 35-39 from Proceedings of a Symposium in Rome Italy Sep. 20-23 1981.
Palmiter et al., Cell vol. 29 pp. 701-710 (1982).
Palmiter et al., Nature 300 pp. 611-615 (1982).
De Greve et al., Nature vol. 300 pp. 752-755 (1982).
Wullems et al., Cell vol. 24 pp. 719-727 (1981).
Brinster et al., Cell 27 pp. 223-231 (1981).
Bürki et al. EMBO J. vol. 1 pp. 127-131 (1982).
Jähner et al., Nature vol 298 pp. 623-628 (1982).
Jaenisch et al., Cell vol. 27 pp. 519-529 (1981).
Wagner et al., PNAS USA vol. 78 pp. 6376-6380 Oct. 1981.
Calos et al., Cell vol. 20 pp. 579-595 Jul. 1980.
Lewis et al., Gene vol. 14 pp. 205-215 (1981).
Bingham et al., Cell vol. 29 pp. 995-1004 Jul. 1982.
Yang et al., PNAS USA vol. 78 pp. 4151-4155 (1981).

*Primary Examiner*—Alvin E. Tanenholtz
*Attorney, Agent, or Firm*—Sughrue, Mion, Zinn Macpeak & Seas

[57] ABSTRACT

A method for incorporating a desired DNA sequence into the genome of a recipient multi-cellular organism comprising:
(1) producing a transposable element of DNA, the element comprising a defined sequence of nucleotide base pairs wherein the defined sequence of nucleotide base pairs comprises at least two sets of target DNA sequences recognizable by transposase and a fragment of DNA, encoding for a structural gene, regulatory gene or other functional DNA, inserted between the sets of target DNA sequences;
(2) incorporating the transposable element produced in (1) above into a cell of a recipient multi-cellular organism; and
(3) causing the transposable element to be affirmatively inserted into the genome of the recipient multi-cellular organism.

The transposable element can additionally become a part of the heritable genome of the recipient multi-cellular organism.

10 Claims, 9 Drawing Figures

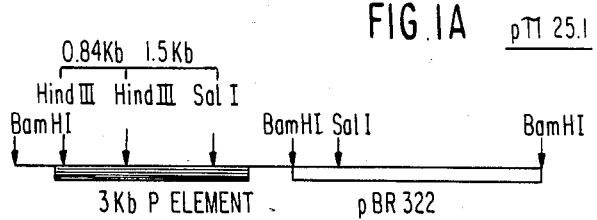
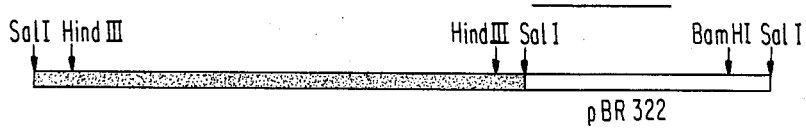
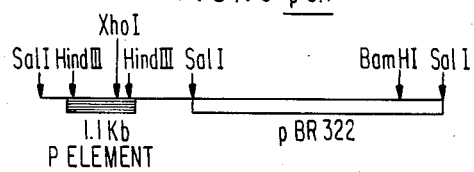
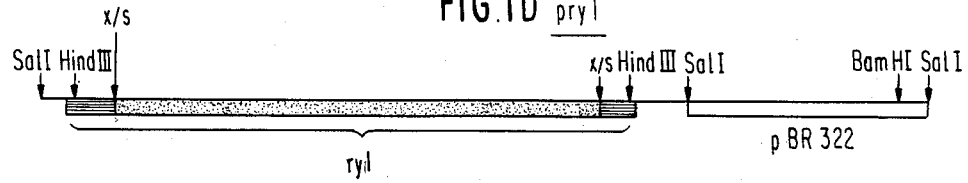
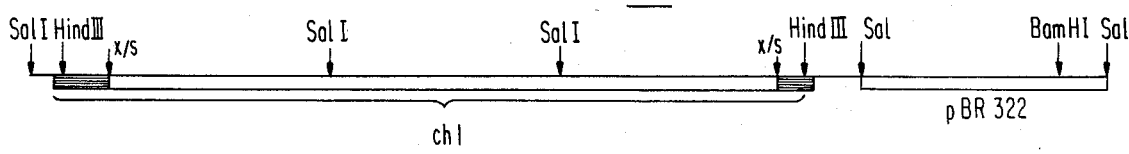

FIG. 3 CONSTRUCTION OF A rosy TRANSPOSON
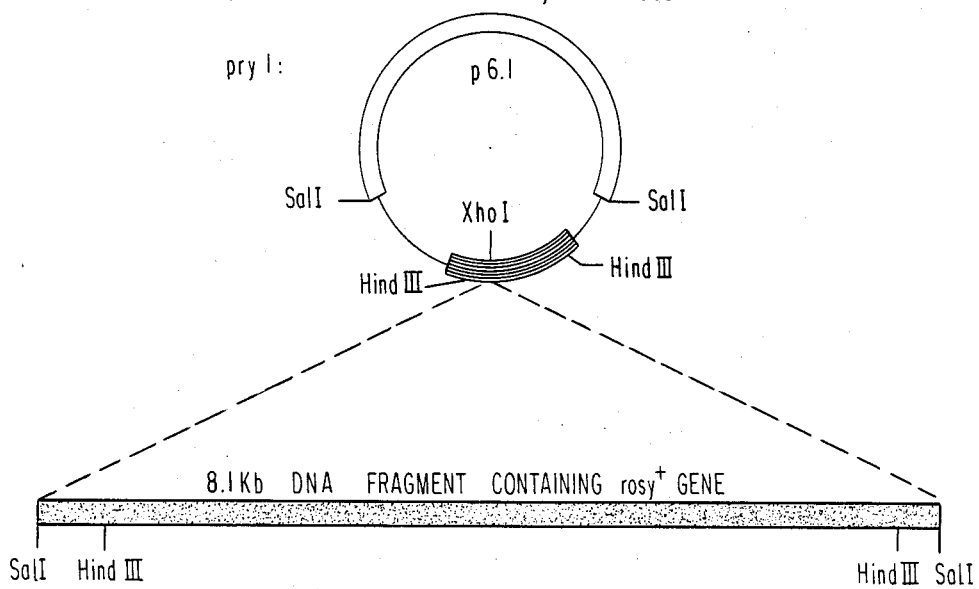
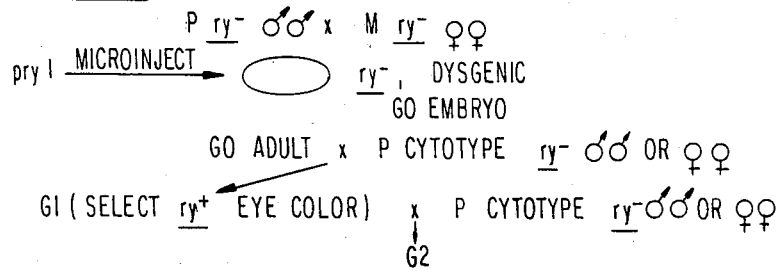
FIG. 4
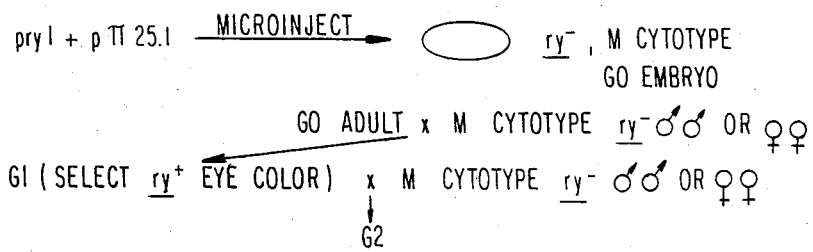
FIG. 5
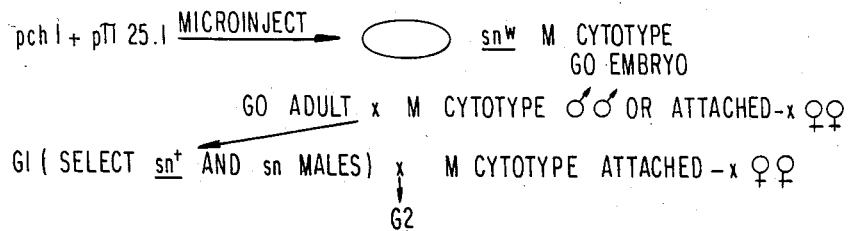
TEST FOR INSERTION OF Ch1 BY
in situ AND NITROCELLULOSE BLOT HYBRIDIZATION 4,670,388

METHOD OF INCORPORATING DNA INTO GENOME OF DROSOPHILA

FIELD OF THE INVENTION

This invention relates to a method for incorporating DNA into a recipient organism. More specifically, this invention relates to a method for incorporating DNA into the genome of a recipient multi-cellular organism. Even more particularly, this invention relates to a method for reproducibly incorporating DNA into the genome of a recipient multi-cellular organism whereby the DNA contains therein a specific nucleotide base pair sequence coding for a regulatory gene, a structural gene or any other DNA sequence capable of altering the biological function(s) of the recipient organism. Further, this invention relates to the expression of the gene to be incorporated not only by the recipient organism but also, in a heritable manner, by the progeny of the organism.

BACKGROUND OF THE INVENTION

The introduction of genetic material into living cells is a common natural occurrence. A wide variety of biological mechanisms have evolved to facilitate, regulate, or prevent the incorporation of new DNA sequences by living cells. Changes in cellular phenotype which result from such events may profoundly influence the characteristics of the cell, including its ability to live, to cause disease, and to produce beneficial or harmful products.

As a consequence, a large amount of effort has been expended in the last 40 years to develop methods by which exogenous genetic information (hereafter referred to as "exogenous DNA", although in some cases the genetic information may be encoded in RNA) can be introduced at will into cells in such a way as to effect desired changes in cellular properties of an organism. These processes of introduction of exogenous DNA into cells are referred to as transformation, transfection, convection, etc. (reviewed in Smith, Danner and Deich, *Ann. Rev. Biochem.*, 50, 41 (1981)). Some of these methods are based on naturally occurring mechanisms of DNA uptake which occur in certain types of bacteria (Avery, McLeod, and McCarty, *J. Exp. Med.*, 79, 137 (1944)), are based on the use of viruses which can infect susoeptible host cells (Zinder and Lederberg, *J. Bacteriology*, 64, 679 (1952)), or are based on bacterial strains of *A. tumafaciens* which can infect and transfer plasmid DNA into the cells of a susceptible plant species (Chilton, et al., *Cell*, 11, 263 (1977)). Other methods for introducing DNA into cells have also been described based on treatment of cells with calcium chloride (Mandel and Higa, *J. Mol. Biol.*, 53, 159 (1970)), the use of polyethylene glycol (PEG) (Chang and Cohen, *Mol. Gen. Genet.*, 168, 111 (1979)), in vitro packaging of DNA in viral coats (Fraenkel-Conrat and Williams, *Proc. Natl. Acad. Sci. USA*, 41, 690 (1955); Hohn and Murray, *Proc. Natl. Acad. Sci. USA*, 74, 3259 (1977)), fusion with cells of DNA-containing liposomes (Fraley et al., *Proc. Natl. Acad. Sci. USA*, 76, 3348 (1979)) or protoplasts (Schaffner, *Proc. Acad. Natl. Acad. Sci. USA*, 77, 2163 (1980)) or by mechanical introduction of DNA by microinjection (Capecchi, *Cell*, 22, 479 (1980)).

In the case of single-celled organisms or the isolated cells of multi-cellular organisms grown in culture, reliable methods for the introduction of exogenous DNA have been described in the literature and are widely used. These include the calcium chloride-mediated uptake of DNA in *E. coli* (Mandel and Higa, *J. Mol. Biol.*, 53, 159 (1970)), polyethylene glycol-mediated uptake in yeast (Hinnen et al., *Proc. Natl. Acad. Sci. USA*, 75, 1929 (1978) and $CaPO_4$-mediated uptake in cultured cells (Graham and van der Eb, *Virology*, 52, 456 (1973); Pellicer et al. *Science*, 209, 1414 (1980)). These methods generally result in the successful introduction of exogenous DNA into a very small fraction of the cells exposed to the exogenous DNA, generally on the order of 1 cell in $10^4$ or less. These methods are therefore used in combination with a methodology for selecting cells into which the exogenous DNA has become incorporated and thereby the cells containing the exogenous DNA have acquired a distinctive property, such as resistance to a particular antibiotic or the ability to utilize a particular growth medium, not possessed by a similar cell which has not incorporated the exogenous DNA. Since even small cultures of bacterial or cultured cells can easily contain $10^5$ or more cells, this approach readily yields at least a few cells which have taken up the exogenous DNA and which can be grown to increase the number of cells containing the exogenous DNA.

It is impractical to apply a similar approach to that which has been widely used for bacteria to the transformation of the cells of multi-cellular animals. The cells of multi-cellular organisms are differentiated and even if the cells in the various intact tissues could be somehow rendered permeable to exogenous DNA uptake, the low frequency of success would be unlikely to result in the acquisition by the organism of any useful characteristics. A more promising approach would be to attempt to transform cells of the germ line (in animals) or of cells (from a plant) which could be regenerated into a complete multi-cellular organism. Germ line cells can not usually be grown in culture, nor can large numbers be easily tested for the presence of exogenous DNA. Consequently, a method of transfer whose efficiency is inherently higher than that of methods widely used with free-living single cells is highly desired.

One approach which might be considered is to use the standard methods of transformation on a cell population. The desired transformed cells are then selected and grown. Subsequently, the transformed cells can be used to generate a complete organism carrying the incorporated DNA. This approach has been widely discussed in the case of plant protoplasts from certain plant species which can be used to regenerate complete whole plants (Steward, *Proc. Royal. Soc. Lond. (Biol.)*, 175, 1 (1970); Vasil and Hildebrant, *Science*, 150, 889 (1975)). The component steps of this process described immediately above have been shown to be feasible in the case of certain lines of mouse teratocarcinoma cells. The uptake and function of DNA in one line of cultured teratocarcinoma cells has been demonstrated (Pellicer et al. *Proc. Natl. Acad. Sci. USA*, 77, 2098 (1980)), and cells of a different line have been used to generate fertile adult mice (Stewart and Mintz, *Proc. Natl. Acad. Sci. USA*, 78, 6314 (1981)). Adult mice containing transformed DNA have yet to be produced in this manner, however.

An alternative approach which has been suggested is to transform cells such as lymphocytes which can repopulate a portion of an adult organism, i.e., bone marrow (Cline et al., *Nature* (Lond.), 284, 422 (1980); Mercola et al. *Science*, 208, 1033 (1980)). The presence of transferred genes in the repopulated bone marrow cells has not yet been demonstrated, however.

Only a very limited number of organisms can be regenerated from cells which can be propagated in vitro in culture. Thus, a far more generally applicable approach would be to directly introduce exogenous DNA into an egg or early embryo of a multi-cellular organism. After development has been completed, the tissues of the resulting organism are then evaluated for the presence of the incorporated exogenous DNA. If germ line cells are among those cells in which exogenous DNA has been retained, some of the progeny may contain the exogenous DNA in all of their cells.

The approach described immediately above requires methods for the introduction of exogenous DNA which are significantly more efficient than those methods used with populations of single cells in culture. In principle, any of a wide variety (see Hinnen et al., (1977); Pellicer et al., (1980); Capecchi, (1980); Fraley et al., (1979); Chang and Cohen, (1979); Hohn and Murray (1977); supra) of presently available techniques could be used to introduce exogenous DNA into eggs, zygotes, or other germ line cells. Certain viruses infect early embryonic cells, including those of the germ line, and viral genetic information may become integrated into the cellular chromosomes. This gives rise to organisms which stably transmit this originally exogenous DNA to their progeny and may display characteristics (i.e., virus production) associated with the originally exogenous DNA (Jaenisch, Proc. Natl. Acad. Sci. USA, 73, 1260 (1976); Harbers et al., Nature (Lond.), 23, 540 (1981)). Specific insertion of DNA by this approach has so far only been used to transfer viral genetic information.

One of the potentially most efficient means of gene transfer into a multi-cellular organism is direct microinjection of exogenous DNA into cell nuclei (Capecchi, Cell, 22, 479 (1980)). Several investigations have recently described the retention of exogenous DNA in adult mice which developed from fertilized eggs that had received DNA injected into one of the pronuclei (Gordon et al., Proc. Natl. Acad. Sci. USA, 77, 7380–84 (1980); Wagner, Stewart and Mintz, Proc. Natl. Acad. Sci. USA, 78, 5016 (1981); Brinster et al., Cell, 27, 223 (1981); Constantini and Lacy, Nature (Lond.), 294, 92 (1981); Wagner et al., Proc. Natl. Acad. Sci. USA, 78, 6376 (1981)). In some of these mice the transferred exogenous DNA was transmitted to its progeny and showed signs of activity. Retention of exogenous DNA during development following injection into fertilized frog eggs has also been reported (Rusconi and Schaffner, Proc. Natl. Acad. Sci. USA, 78, 5051 (1981)).

The currently available conventional methods for introducing exogenous DNA into eukaryotic cells and organisms as described above suffer from numerous difficulties which limit their use. Some of the important limitations are set forth below:

(1) It is not possible in any of these methods to precisely control and to vary at will what exogenous DNA sequences are transferred into the genome of the recipient;

(2) Those exogenous DNA sequences which are transferred into the genome of the recipient have often undergone changes in structure and/or number during the process of transfer or during subsequent propagation of the recipient;

(3) The transfer of DNA sequences into the genome of a recipient is not known to depend on the presence of catalytic factors which are not present in the recipient cell itself, and, thus, it is not likely to be possible to limit transfer of DNA sequences to specific tissues or developmental stages of the recipient;

(4) Transfer of DNA sequences into the genome of the recipient occurs at low frequencies in most of the conventional methods; and (5) Genes introduced into multicellular organisms by conventional methods have never been shown to be subject to normal developmental controls, however, this is likely to be a prerequisite for most applications in such multicellular organisms.

Accordingly, development of a system which overcomes or significantly reduces the above difficulties of conventional methods of DNA incorporation based on a unique utilization of the properties of natural biological entities known as transposons or transposable elements (reviewed in Calos and Miller, Cell, 20, 579 (1980)) is desired.

SUMMARY OF THE INVENTION

An object of this invention is to provide a method for introduction of DNA into living cells, particularly into cells of multi-cellular organisms.

Another object of this invention is to provide a method whereby DNA can be incorporated into the genome of an organism, particularly a multi-cellular organism.

An even further object of this invention is to provide a method for the introduction of DNA into multi-cellular organisms in an efficient manner.

Also an object of this invention is to provide a method of incorporation of DNA into a multi-cellular organism wherein this originally DNA is heritably transmitted to progeny of the multi-cellular organism.

An additional object of this invention is to provide a method for incorporation of DNA into the oells of a multi-cellular organism wherein the incorporation of DNA is reproducible, controllable and predictable.

Another object of this invention is to provide a method for the incorporation of DNA into the cells of a multi-cellular organism wherein genes within the DNA come under the normal developmental controls of the recipient organism.

This invention is based on a discovery that the properties of naturally occurring biological entities, known in the art as transposable elements or "transposons" can be utilized to achieve the incorporation of DNA into the cells of a multi-cellular organism.

For the purposes of this disclosure, a transposable element or a transposon (used interchangeably herein) refers to a DNA or RNA sequence which is defined as follows: a defined sequence of nucleotides which under appropriate conditions can cause an identical or equivalent sequence of nucleotides to be inserted at one or a variety of sites into the DNA of a host cell in which it resides. Further, certain nucleic acid sequences occur naturally in extracellular particles known as viruses. Some virus nucleic acids such as bacteriophage λ and Mu (Kleckner, Ann. Rev. Genet., 15, 341 (1981)) and eukaryotic retroviruses (Temin, Cell, 21, 599 (1980)) are considered to have the capability of functioning as transposable elements following introduction into cells and hence are to be considered within the scope of these terms as used herein.

Accordingly, this invention in one embodiment provides a method for incorporating a desired DNA sequence into the genome of a recipient multi-cellular organism comprising:

(1) producing a transposable element of DNA the element comprising a defined sequence of nucleotide base pairs wherein the defined sequence of nucleotide base pairs comprises at least two sets of target DNA sequences recognizable by transposase and a fragment of DNA, encoding for a structural gene, a regulatory gene or other functional DNA, inserted between the sets of target DNA sequences;

(2) introducing the transposable element produced in (1) above into at least one cell of a recipient multi-cellular organism; and (3) causing the transposable element to be affirmatively inserted into the genome of the recipient multi-cellular organism.

In another embodiment, this transposable element additionally becomes a part of the heritable genome of the recipient multi-cellular organism.

BRIEF DESCRIPTION OF THE ACCOMPANYING DRAWINGS

FIG. 1 shows the restriction enzyme map, in linear form, of relevant plasmids which can be used in this invention, as demonstrated in the Examples given hereinafter; FIG. 1A shows the map for plasmid p$\pi$25.1; FIG. 1B shows the plasmid pDm2844S8.5; FIG. 1C shows the plasmid p6.1; FIG. 1D shows the pryI plasmid; the FIG. 1E shows the pchI plasmid. In FIGS. 1D and 1E "X/S" indicates the nucleotide sequence created by the ligation of SalI and XhoI generated termini.

FIG. 2 shows the experimental protocol used in Example 1 given hereinafter, wherein an intact P-element transposon was transferred into the germline chromosomes of sn$^2$ embroys of fruit flies (*Drosophila melanogaster*).

FIG. 3 illustrates the construction of plasmid pyrI of FIG. 1D containing the rosy$^+$ transposon ryI.

FIG. 4 shows the experimental protocol used in Example 2 given hereinafter, wherein a rosy$^+$ gene located in the transposon ryI is transferred into the germline chromosomes of rosy mutant fruit fly embryos.

FIG. 5 illustrates the experimental protocol used in Example 3 given hereinafter, wherein a segment of DNA containing chorion genes located in the transposon chI, which is present on the plasmid pchI, was transferred into sn$^w$ fluit fly embryos.

DETAILED DESCRIPTION OF THE INVENTION

Naturally occurring biological entities known as transposable elements or transposons are described in Calos and Miller, *Cell*, 20, 579 (1980). These transposons have the ability to change their position within the genome of their host as discrete entities. In the case of one large subclass of transposable elements, this movement is both catalyzed by and requires a particular enzyme (transposase) which is encoded by the transposon and is specific for that particular element and closely related elements. This enzyme or transposase acts at a specific nucleotide base pair sequence which exists at the ends of the transposon (hereinafter this specific nucleotide base pair sequence is designated a "target DNA sequence") and catalyzes the specific insertion of the sequence of nucleotide base pairs, hereinafter "DNA sequence", present between these specific terminal target DNA sequences, to a new site in the genome. Thus, the ability of the transposon to be inserted into a genome site can be controlled by modulating the level of or structure of the transposase or the nucleotide base pair sequence of the specific sites at which the transposase acts. Furthermore, the base pair sequence of the DNA encoding the transposase need not be present on the same DNA molecule as the target DNA sequence on which it acts.

It has now been discovered that transposons can be used to introduce exogenous DNA fragments into a multi-cellular organism genome. This exogenous DNA can contain therein a specific nucleotide base pair sequence coding for a structural gene, a regulatory gene, or any other DNA sequence capable of altering the biological function(s) of the recipient organism. As used herein, a structural gene is a gene which codes for an RNA or protein product, e.g., a ribosomal RNA or a globin polypeptide. A regulatory gene is a gene which controls or influences the expression of structural genes or other regulatory genes. Examples of other DNA sequences with biological functions would include origin sequences for DNA replication, specific DNA sequences recognized by a protein such as the binding site for a regulatory gene product, or enhancer sequences.

The ability to use transposons has been experimentally demonstrated in this invention by using *Drosophila melanogaster* as a multi-cellular system as described in greater detail hereinafter. A series of derivatives of the P family of transposons of *Drosophila melanogaster* have been isolated and characterized. This invention is considered to be broadly applicable to other multi-cellular organisms.

In general in the method of this invention, a DNA plasmid is produced by standard methods of restriction enzyme cleavage, ligation and molecular cloning (described in detail below and in R. Wu, Ed. *Methods in Enzymology*, Vol. 68, Academic Press, New York (1979), the disclosure of which is incorporated herein by reference) and has the following properties: (1) it contains DNA sequences ("vector sequences") which confer on the plasmid the ability to replicate in bacteria; (2) it also contains additional DNA sequences which comprise a transposable element, i.e., two target DNA sequences which can be acted upon by transposase, and located between these target DNA sequences the particular exogenous DNA sequences, such as those coding for particular protein(s), whose transfer into a eukaryotic cell chromosome is desired. The function of the vector sequences is to allow the production of adequate amounts of highly pure DNA containing the transposable element by standard molecular cloning techniques. Many vector-host combinations with the desired properties have been described in the art, including the plasmid pBR322/*E. coli* (Bolivar et al., *Gene* 2, 95 (1977)); bacteriophage Charon 4/*E. coli* (Blattner et al., *Science*, 196, 161 (1977)); cosmid MUA-3/ *E. coli* (Meyerowtiz et al., *Gene*, 11, 271 (1980)) and YEp6/ *S. cerevisiae* (Struhl et al., *Proc. Natl. Acad. Sci. USA*, 76, 1035 (1979)) and are useful herein, the disclosures of which are all incorporated herein by reference. The function of the transposable element sequences is to transpose, along with any DNA sequences located between the target DNA sequences which define its termini, into the chromosomes of a eukaryotic cell under appropriate conditions and in the presence of transposase.

The transposon may vary in size from just the few dozen nucleotides required to specify two target DNA sequences, to transposons containing hundreds of thousands of additional nucleotides. The size of the transposon which can be used in this invention is not limited and is dictated basically only by the length of the nucleotide sequence whose transfer into a eukaryotic chromosome is desired. Transposons smaller than about 40 kb (kilobases) are easier to construct than larger ones, but no absolute size limits exist.

The construction of the DNA plasmid containing vector and transposon sequences is accomplished by the following general steps. Purified DNAs containing desired component nucleotide sequences as well as extraneous sequences are cleaved with restriction endonucleases that recognize specific nucleotide sequences (reviewed in Roberts, *Critical Reviews Biochem.*, 4, 123 (1976), the disclosure of which is incorporated herein by reference). For example, restriction endonuclease Eco RI cleaves at 5'-GAATTC-3', Bam HI cleaves at 5'-GGATCC-3', Hind III cleaves at 5'-AAGCTT-3', Sal I cleaves at 5'-GTCGAC-3', Xho I cleaves at 5'-CTCGAG-3' and Hae III cleaves at 5'-GGCC-3'. Fragments containing the desired nucleotide sequences are separated from unwanted DNA fragments of different size using conventional methods, e.g., by agarose gel electrophoresis. The desired DNA fragments are excised from the gel and ligated together in the appropriate configuration so that a circular DNA containing vector sequences and the desired transposon sequence is produced. For example, DNA ligase from T4 bacteriophage or *E. coli* cells can be used for ligating DNA fragments. FIG. 3 describes an example of such a plasmid construction that was used in Example 2 described hereinafter. The circular DNA molecules so constructed are used to transform *E. coli* cells. Once inside the *E. coli*, the circular DNA molecules replicate and their number is amplified during *E. coli* cell growth. The plasmid DNA purified from the transformed *E. coli* cells provides an adequate supply of the specifically constructed DNA for use in the subsequent steps of this invention. The procedures of cleavage, plasmid construction, cell transformation and plasmid production involved in these steps are well known to one skilled in the art and the enzymes required for restriction and ligation are available commercially. (See, for example, R. Wu, Ed., *Methods in Enzymology*, Vol. 68, Academic Press, N.Y. (1979); T. Maniatis, E. F. Fritsch and J. Sambrook, *Molecular Cloning: A Laboratory Manual*, Cold Spring Harbor Laboratory Press, Cold Spring Harbor, N.Y. (1982); Catalog 1982-83, New England Biolabs, Inc.; Catalog 1982-83, Bethesda Research Laboratories, Inc., the disclosures of which are herein incorporated by reference).

A second DNA molecule is constructed, another plasmid for example, which contains the DNA sequences encoding the transposase that recognizes the target DNA sequences at the termini of the transposon on the first plasmid. The exact chemical nature of the transposase that acts on transposable elements is not clearly defined. While not desiring to be bound, generally the transposase consists of one or a few proteins, encoded by a defined segment of DNA, which must be present for transposition to occur. The detailed molecular mechanism of the transposition process is also not yet clarified, and again while not desiring to be bound, the process is presumed to involve ubiquitous cellular enzymes such as nucleases, polymerases and ligases as well as transposase. Present knowledge concerning the nature of target DNA sequences, transposases, host enzymes and transposition mechanisms has been reviewed recently (Kleckner, *Ann. Rev. Genet.*, 15, 341 (1981), the disclosure of which is incorporated by reference). Knowledge of the exact nature of transposase, of the cellular enzymes or of the mechanistic details of the transposition process is not important for the purposes of this invention. The transposition of a transposable element can be controlled by regulating the availability of the DNA sequences encoding transposase; in the presence of these sequences transposition occurs, in their absence it cannot. In the examples described hereinafter the sequences encoding transposase are located on the 3 kb P element in plasmid pπ25.1 (see FIG. 1A).

When the first plasmid containing the target DNA sequences and the second plasmid encoding transposase are delivered together into the recipient cell(s), a functional transposase is produced by the second plasmid and acts, in conjunction with factors present in the recipient cell, to catalyze the transfer of precisely those nucleotide sequences located on the first plasmid between and including the target sequences into the genome of the recipient cell. It should be noted that the target DNA sequences have a polarity such that in a circular DNA molecule, as shown in FIGS 1D and 1E, only the DNA sequences labeled ry1 or ch1 are transferred. The remaining DNA sequences (vector and flanking sequences), are not so transferred.

After transposition of the transposon into the chromosome of the recipient cell has occurred, the transposon will undergo replication and be stably inherited in both daughters of the cell at division and in subsequent divisions. If the cell is a germline cell from a multicellular organism, the transposon will be inherited in some of the progeny of that organism. The plasmid DNAs which were delivered to the recipient cell cannot replicate in a stable manner. They will be diluted to insignificant levels during subsequent cell divisions. They may also undergo degradation by host nucleases. Hence, they will not be stably inherited in the progeny of a multicellular organism.

Since transposase can only be produced in response to the DNA sequences encoding it on the second plasmid, the transposase level present in the recipient cell will decrease as cell division occurs and will soon fall below levels at which it can function in promoting transposition. Thus, while a transposon which has integrated into a recipient cell may be exposed to transposase for a brief period of time, and may rarely undergo a second transposition event, the transposon will soon be inherited in cells which lack functional levels of transposase. Thereafter, as long as transposase is absent, the transposon will remain as a stable and heritable genomic component of the recipient cell.

The method of this invention is not dependent on the technique used for delivering the two plasmids containing the target sequences and the DNA sequences encoding the transposase into the recipient cell. The delivery can be accomplished by any of a variety of conventional methods suitable for introducing exogenous DNA into the cytoplasm or nucleus of cells (see Chang and Cohen (1979); Capecchi (1980); Fraley et al. (1979); Hinnen et al (1977); Pellicer et al. (1980); Hohn and Murray (1977), supra, the disclosures of which are incorporated herein by reference). The preferred method will vary with recipient cell type, developmental state, etc., and can be determined empirically in each case by one skilled in the art using routine techniques.

This method of this invention is therefore applicable to all transposons in which a specific enzyme acts on specific DNA target sequences in conjunction with recipient cell factors to catalyze the insertion of a sequence between the specific target DNA sequence into a chromosome of the recipient cell. The method of this invention provides the ability to solve problems of conventional gene transfer methods described above. The method of this invention provides, among others, the following advantages:

(1) The specific DNA sequences transferred are defined and are those sequences which are located between the target DNA sequences for the element-encoded enzyme(s).

(2) Because insertion of DNA sequences by this method is a specifically catalyzed process, rearrangements of DNA sequences during the process of insertion is rare, in contrast to the situation in the prior art.

(3) The inserted DNA sequences are stably inherited in subsequent generations.

(4) Since the insertion process requires production of transposase, transfer can only take place when transposase is produced in suitable amounts. In the absence of transposase, the inserted DNA sequences are stable. The production of transposase appears susceptible to experimental control. Using conventional techniques (Wu (1979), supra; Maniutis et al. (1982), supra) DNA encoding transposase could be ligated to DNA from a gene with the desired developmental activity. The resulting fused gene might retain the pattern of developmental expression characteristics of the latter gene, and still produce a protein with transposase activity. In this way, the insertion of a transposable element may be limited to only certain types of cells in a mixed population all of which have been exposed to the exogenous DNA.

(5) The frequency of exogenous genomic incorporation in the recipient cell in this process is high.

(6) DNA sequences transferred by the method of this invention frequently come under the normal developmental controls of the recipient multicellular organism (as shown by Example 2 hereinafter).

The method of DNA sequence and/or gene transfer, as outlined above, has broad utility, with applications in agriculture, medicine, and industrial production where reliable methods for introducing exogenous DNA into the genomes of plants and animals are required for the production of modified genetic properties within these organisms.

A safe and efficient means of controlling many insects that are serious agricultural pests is of great economic significance. One approach to the control of a variety of injurious insects, including the Mediterranean fruit fly (*Ceratitis crepitata*), is the release of large numbers of sterile males produced by irradiating laboratory-raised flies to induce sterility. The method of the present invention could be used to efficiently product large populations of sterile male fruit flies, as well as females, all of whose male progeny would be sterile and whose female progeny would, like themselves, produce exclusively sterile males. Release of a small number of such sterile flies produced by the method of this invention would be as effective in reducing the numbers of a wild population of fruit flies as release of a much larger number of sterile males conventionally produced by irradiation, since new generations of sterile males will be produced by matings between wild (fertile) males and the released females or their female descendants.

The production of such sterile fruit flies would involve the use of genes which cause dominant male sterility such as the $B2t^D$ gene (Kemphues et al., *Proc. Natl. Acad. Sci. USA*, 76, 3391 (1979)) in the laboratory fruit fly *Drosophila melanogaster*. This gene, which codes for a $\beta$-tubulin protein expressed only in the testis, would be isolated, cloned and then inserted into a transposon capable of transposition in the Mediterranean fruit fly. Unlike many other applications where stability of the transferred DNA is desirable, the choice of transposon and the details of the construction would be arranged to insure that the transposons carrying the $B2t^D$ gene remained active after transfer so that multiple copies of the transposon per genome would accumulate. This would insure that matings between female flies carrying the transposons and fertile male flies did not produce any fertile male offspring due to meiotic segregation of the transposons. Once such a stock was established, it could be maintained by mating females to males from a separate stock lacking the transposons. Any male progeny produced by such a cross would inherit one or more transposons and hence would be completely sterile. Female progeny would also inherit transposons and would continue to pass them to their male and female progeny. (If the *D. melanogaster* $B2t^D$ gene did not function in *Ceratitis crepitata*, it could be modified to so function prior to incorporation into the transposon.) Similar sterility inducing transposons could be produced using other dominant sterile genes of *D. melanogaster* such as Fs(2)D (see Lindsley and Grell, *Carnegie Inst. Publication* No. 627 (1968)).

Further, many foods derived from plants are deficient in certain amino acids. For example, the edible protein from corn is deficient in the amino acids lysine and tryptophan. The French bean is low in its content of cysteine and methionine. If the amino acid composition of the proteins of these plants could be altered to produce a protein mixture more nutritious to animals and humans, the value of the plant as a food source would greatly increase. In many plants, such as corn or beans, a large proportion of the edible protein arises from a single family of polypeptides (zein in the case of corn; phaseolin in the case of the French bean). Thus, reinsertion into the plant genome of additional functional zein or phaseolin genes modified by in vitro mutagenesis (e.g., as described in Shortle et al., *Ann. Rev. Genet.*, 15, 265 (1981)) to encode proteins with a more desirable amino acid composition would increase the nutritional value of plants such as beans and corn. DNA sequences encoding zein and phaseolin have been isolated by recombinant DNA techniques as described in Wienand et al., *Mol. Gen. Genet.* 182, 440–444 (1981); Lewis et al., *Gene* 14, 205–15 (1981); Sun et al. *Nature* 289, 37 (1981)) and these DNA sequences will be utilizable in the process of this invention.

Specifically, by molecular cloning techniques, modified storage protein genes could be inserted between appropriate target sequences. The storage protein gene transposons which result could then be introduced into the genome of protoplast cells of the same or other plant species. Cells incorporating one or more copies of the transposons would be used to regenerate plants, some of which would utilize the storage protein genes located within the transposons at sufficient levels to significantly alter the amino acid composition of the seeds in a beneficial manner. In some cases, concomitant transfer of a second gene conferring a recognizable phenotype on the recipient protoplasts could be used to identify those cells which have incorporated the exogenous DNA by analogy to Example 3, given hereinafter.

Because similar storage proteins in other plants also tend to be produced in large amounts, the messenger RNAs encoding for these proteins and the genes encoding for these proteins should be generally amenable to isolation by standard and conventional recombinant DNA techniques. (Maniatis et al. (1982); supra). The process of this invention has application to utilization of these sequences and genes, as well.

Numerous medical disorders are known to be due to defects in single genes, for example, thalasemias and sickle cell anemia. These disorders should be treatable by introducing a functional non-defective copy of the affected gene into the appropriate cells or organ of a patient having such a disorder. For example, patients suffering from certain forms of thalasemia have been shown to lack functional genes for either $\alpha$- or $\beta$-globin. Functional genes for either $\alpha$- or $\beta$-globin are available in cloned form and could be introduced in bone marrow cells, which were removed from the patient, by the method of this invention. The population of bone marrow cells, some of which had taken up the functional globin gene transposons into their chromosomes, using the process of this invention, could be reintroduced into the patient following treatment to deplete the cells in the marrow. In some cases, concomitant transfer of a second gene conferring recognizable properties on recipient cells could be used to identify those cells which had incorporated the exogenous DNA by analogy to Example 3, given hereinafter. Such transplantation of bone marrow cells is a feasible procedure which is currently used in the treatment of several hematological disorders, notably leukemia, but its usefulness is presently severely limited due to immune rejection of cells derived from a foreign donor source. Reintroduction of the patient's own cells, modified as would occur using this invention, would pose no such immune rejection problem. The patient's own cells containing normal globin genes introduced using the process of this invention should produce normal hemoglobin and thereby alleviate the symptoms of the thalassemia. A permanent cure for the affected individual could result if a sufficient number of stem cells containing the normal globin gene repopulate the marrow.

The DNA fragment located between the sets of target sequences comprises nucleotide base pair sequences encoding, for example, protein recognition sites such as protein binding on cleavage sites, origin of DNA replication sites, enhancer sequences, and RNA.

The following examples are given to illustrate the present invention in greater delail, but they are not to be construed as limiting the scope of this invention.

In the following, the fruit fly Drosophila melanogaster was used merely as a representative multi-cellular organism to demonstrate the utility of the process of this invention to multi-cellular organisms.

In the specific examples shown below exogenous DNA was transferred into the germ line of Drosophila melanogaster. A specific transposable element known as the "P factor" (See Engels, Cold Spring Harbor Symp., 45, 561 (1981), the discosure of which is incorporated herein by reference) was used. This transposable element displays the properties expected for a transposon which codes for a protein or series of proteins that is necessary for the precise transposition of DNA located between defined terminal target DNA sequences.

The presence of P factors in the genome of a Drosophila embryo derived from female which lacked such factors (hereinafter denoted as an M strain female) gives rise to a specific set of phenotypes limited largely to the germline called "hybrid dysgenesis". These phenotypes include temperature-sensitive sterility, male recombination, site specific chromosome rearrangement and destabilization of certain mutant phenotypes. One of the most sensitive phenotypic assays for dysgenesis and hence the P factor is the appearance of hypermutability at certain genetic loci, in particular the singed (sn) locus (Engels, Cold Spring Harbor Symp., 45, 561 (1981)). By assaying for such hypermutability and by direct chemica tests based on nucleic acid hybridization, P factors have now been experimentally shown to modulate their own insertion into the chromosomes of germ line cells following injection of recombinant plasmed DNA containing a P factor and flanking target DNA sequences into 0–90-minute-old Drosophila embryos. These germ cells give rise to strains of flies which stably inherit intact P factors at defined chromosomal sites, and which continue to display sn hypermutability indicating that the transferred P factor is functional, as set forth in Example 1 hereinafter.

The controlled insertion of a defined gene, rosy (ry), which codes for the enzyme xanthine dehydrogenase, can also be carried out using this invention, as shown by Example 2 hereinafter. The absence of a functional rosy gene gives rise to flies with abnormal rosy coored eye pigmentation. DNA coding for the wild-type rosy gene was inserted between the terminal repeats of a P factor to create the rosy transposon ry1, and injected into embryos homozyqous for a partial deletion of the normal rosy gene ($ry^{60}$). A complete P factor was injected simultaneously to provide the transposase function (not producible by the altered P factor in ry1). Twenty to 50 percent of the resulting flies produced wild-type ($ry^+$) progeny. These progeny were shown to be the result of the insertion of one or two intact copies of ry1 into the chromosomes where expression of this gene gives rise to the wild-type eye color phenotype. Assays of the activity of the transferred gene showed that it was expressed in normal amounts and in the appropriate tissues of the progeny flies and in succeeding generations.

Finally, with lhis system DNA sequences which do not themselves confer a recognizable property upon the recipient cells have been demonstrated to be efficiently introduced into the genomes of recipient cells by the method of this invention. For example, a fragment of DNA containing two genes encoding eggshell proteins was introduced into the $sn^w$ strain, as shown in Exampe 3 hereinafter.

The genetic symbols used herein are set forth in Table 1 below.

TABLE 1

| Genetic Symbols | Meaning |
| --- | --- |
| sn | singed bristles, X chromosome |
| $sn^w$ | a "weak" allele of singed in which bristles are slightly reduced in length and ocassionally bent |
| $sn^e$ | an "extreme" allele of singed in which bristles are severely reduced in length and highly twisted in appearance |
| ry | rosy eye color, 3rd chromosome, codes for xanthine dehydrogenase (XDH) |
| $ry^{60}$ | an allele of rosy which has undergone a 0.9 kilobase (kb) deletion, destroying all activity of the XDH gene |
| $ry^{42}$ | an allele of rosy lacking detectable XDH activity |
| M | an M strain is a Drosophila strain which lacks P factors in its |

TABLE 1-continued

| Genetic Symbols | Meaning |
|---|---|
| | chromosomes (see Engels, W., Genet. Res. 33, 137 (1979)) |

Note: For more details on genetic symbols and characterization see Lindsley and Grell, Genetic Variation in Drosophila melanogaster, Carnegie Institute of Washington Publication No. 627 (1968).

EXAMPLE 1

Introduction of Complete P Element Transposons Into the Drosophila melanogaster Genome Transformation of $sn^w$ Embryos with p$\pi$25.1 DNA The following example demonstrates that intaot P factor DNA, cloned on a plasmid, can be transposed into the genome of an appropriate host embryo (lacking endogenous P factors). FIG. 2 illustrates the experimental protocol used in this example.

In order to assay for the presence of a functional P factor, the host embryos were homozygous for the "singed-weak" allele ($sn^w$) of the singed locus (Engels, *Proc. Natl. Acad. Sci. USA*, 76, 4011 (1979)). The singed gene in this allele is parlly inactivated due to the presence of an inserlion of DNA flanked by the terminal sequences recognized by the P factor products. Hypermutability results from excision or further rearrangement of this insert under conditions of hybrid dysgenesis. The $sn^w$ strain used in these experiments ("$sn^w$ M strain") had been backcrossed repeatedly to flies lacking chromosomal P elements, until no active P elements remained. When P factor-coded products are reintroduced into such a strain, $sn^w$ allele mutates at rates as high as 50%. Therefore if P factors injected into such embryos are able to function, products derived from them (in conjunction with host factors) would result in a detectable rate of $sn^w$ mutation. Such an event is recognized by the resulting change in appearance of the bristles in progeny of the injected flies. Since P factor activity is mainly limited to germine cells, changes in the bristles of the G1 generation flies are expected. If a P factor were to become integrated and be stably transmitted, $sn^w$ hypermutability should persist in future generations. Control experiments showed that hypermutability in the $sn^w$ strain was never observed in the absence of a functional P factor.

The DNA used in these experiments was the recombinant plasmid p$\pi$25.1 (see FIG. 1A) (prepared as described in Levis et al., *Cell*, 21, 581 (1980). Plasmid p$\pi$25.1 consists of a 4.5 kb Bam HI fragment of Drosophila DNA derived from a portion of the X-chromosome of a strain known to contain numerous P factors (Engels and Preston, *Genetics*, 92, 161 (1979)) cloned in the plasmid pBR322 (Bolivar et al. *Gene*, 2, 95 (1977)). This Bam HI fragment contains a presumptive P factor surrounded by flanking chromosomal DNA.

In this example, embryos from the $sn^w$ M strain were injected with a variety of concentrations of p$\pi$25.1 DNA. Microinjection was carried out by a modification of the methods described by Van Deusen, *J. Embry. Exp. Morph.*, 37 173 (1976)). Drosophila flies of the $sn^w$ strain were maintained in plastic population cages at 21°–23° C. Embryos were collected on lightly yeasted agar plates for one hour, then transferred to 17°–18° C., the temperature of all subsequent operations. Chorions were removed on double-stick tape and the embryos aligned in a row on a 22×40 mm cover-slip such that all but their posterior ends were attached to a small piece of doube-slick tape.

The coverslip containing the embryos was dessicated in a petri dish containing $CaCl_2$ (commercially available Drierite) for 5–10 minutes, and then the embryos were covered with heavy fluorocarbon oil (No. 405 produced by Halocarbon Products) to minimize further drying. The cover-slip was mounted on the stage of an inverted microscope (Zeiss, Invertoscope D phase optics) and each embryo was injected with of its volume of a solution containing plasmid DNA in a buffer consisting of 5 mM KCl and 0.1 mM $Na_3PO_4$ pH 6.8. Injection needles were pulled from glass tubing (Drummond, 25 $\mu$l "Microcaps") with a pipette puller Model 700C (commercially available from David Kopf). The tips were broken to obtain a sharp point with an external diameter of 1 to 5 microns. Injection at the posterior tip of the embryo was carried out using a Leitz micromanipulator. After injection, the embryos were maintained in a humidified chamber at 17°–18° C. Hatched larvae were removed from the oil and placed on standard Drosophila cornmeal-molasses-yeast medium with subsequent development at 21°–23° C.

Surviving embryos which developed into fertile adult flies were mated as illustrated in FIG. 2 (G0 generation). Progeny males (G1 generation) were examined with regard to bristle phenotype.

Table 2 below summarizes the results obtained in this example and demonstrates the effect of DNA concentration on the production of injected flies that produced exceptional singed G1 progeny.

TABLE 2

Production of Germline Mutable Flies by the Injection of p$\pi$25.1 DNA into Early Drosophila Embryos

| Run No. | p$\pi$25.1 DNA Concentration ($\mu$g/ml) | Number of Embryos Injected | Number of Fertile Adults | Number Yielding Mutable Progeny |
|---|---|---|---|---|
| 1 | 0 | 183 | 34 | 0 (0%) |
| 2 | 0.1 | 184 | 30 | 0 (0%) |
| 3 | 10 | 397 | 43 | 2 (5%) |
| 4 | 100 | 363 | 56 | 27 (48%) |
| 5 | 1000 | 522 | 100 | 2 (2%) |

The above results show that while a few G0 individuals produced exceptional singed G1 progeny following injection with p$\pi$25.1 DNA at 1000 $\mu$g/ml or 10 $\mu$g/ml, injection of this DNA at 100 $\mu$g/ml caused germline mutability in 7% of all injected embryos, or nearly 50% of surviving fertile adults. No mutable G0 adults resulted from the injection of DNA lacking P factors. Table 3 illustrates the extent of mutability observed in G1 offspring of G0 embryos from Run Nos. 3, 4 and 5.

TABLE 3

Phenotype of Male Progeny of Injected Embryos Displaying Germline Mosaicism

| Embryo | Progeny Phenotype | | |
|---|---|---|---|
| | sn | $sn^w$ | $sn^e$ |
| 101 | 5 | 34 | — |
| 102 | 6 | 81 | — |
| 201 | 3 | 31 | 6 |
| 202 | 3 | 38 | 3 |
| 203 | 1 | 114 | — |
| 204 | 1 | 33 | — |
| 205 | 3 | 70 | 11 |
| 206 | — | 117 | 1 |
| 207 | 1 | 67 | 5 |
| 208 | 1 | 119 | 1 |

TABLE 3-continued

Phenotype of Male Progeny of Injected Embryos Displaying Germline Mosaicism

| Embryo | sn | Progeny Phenotype sn$^w$ | sn$^e$ |
|---|---|---|---|
| 209 | 1 | 45 | 1 |
| 210 | 2 | 63 | 4 |
| 211 | 1 | 42 | 2 |
| 212 | — | 5 | 1 |
| 213 | 2 | 32 | 22 |
| 214 | 10 | 53 | 3 |
| 215 | 7 | 66 | — |
| 216 | 5 | 38 | — |
| 217 | 2 | 21 | — |
| 218 | — | 57 | 4 |
| 219 | 6 | 36 | 3 |
| 220 | 3 | 59 | — |
| 221 | 4 | 31 | 1 |
| 222 | 2 | 42 | — |
| 223 | 1 | 48 | 1 |
| 224 | 1 | 43 | — |
| 225 | — | 30 | 4 |
| 226 | 5 | 42 | — |
| 227 | — | 44 | 1 |
| 301 | — | 17 | 1 |
| 302 | 2 | 159 | — |

That these exceptional progeny were indeed the result of the activity of the P factor on p$\pi$25.1 DNA was verified in a variety of ways.

Individual G1 male progeny of mutable G0 flies were mated to attached-X females and the singed phenotype of their male offspring (G2 generation; see FIG. 2) was determined. Examples of these analyses are contained in Table 4 below. It was observed that many of the tested G1 males were themselves mutable, yielding G2 progeny males with different singed phenotypes than expected. This provides genetic evidence for the presence of one or more functional heritable P elements in such G1 males. Examination of the singed phenotypes of successive generations of males which had been crossed to attached-X females demonstrated that the property of mutability was transmitted faithfully by mutable G1 males.

TABLE 4

Induction of sn$^w$ Mutability by Individual Male G1 Progeny of Mutable G0 Flies

| Individual | sn Phenotype | sn$^+$ | sn$^w$ | sn$^e$ |
|---|---|---|---|---|
| 101-1 | + | 110 | — | — |
| 101-2 | + | 160 | — | — |
| 101-3 | + | 209 | — | 16 |
| 101-4 | + | 54 | — | — |
| 101-5 | + | 124 | — | — |
| 301-1 | e | 5 | — | 329 |
| 301-2 | w | — | 100 | — |
| 301-3 | w | 12 | 227 | 13 |
| 301-4 | w | — | 287 | — |

G1 male progeny of the same G0 injected fly are numbered consecutively using the same identifying number as in Table 3.

To demonstrate the presence of new P factor-complementary sequences in the hypermutable strains, chromosomes were prepared from larval salivary glands and hybridized in situ with $^3$H-labelled probe complementary to p$\pi$25.1 DNA. (A detailed description of this hybridization technique is given in Pardue and Gall, *Methods in Cell Biology*, 10, (1975), and in Spradling, *Cell*, 27, 193 (1981)). All the hypermutable strains contained one or a few sites of hybridization on the chromosomes not found in the host strain.

Further evidence that intact P elements had transposed from the injected plasmid DNA into the chromosomes of the germline cells which gave rise to the mutable strains was obtained by gel transfer experiments. (A detailed description of this gel transfer technique is given in Southern, *J. Mol. Biol.*, 98, 503 (1975) and in Spradling, Cell, 27, (1981)).

Two of the G1 male progeny of 301 (301-1 and 301-3) showed continued mutability while a sibling male (301-2) was phenotypically stable (see Table 4). Likewise, one G1 male progeny of G0 embryo 101 was mutable (101-3) and two were stable (101-2 and 101-4). DNA was prepared from the sn$^w$ M host strain, and from the G2 male progeny of the six G1 males. The presence of one or more complete P elements was assayed by digesting the DNAs with Hind III and Sal I, transferring the digests to nitrocellulose paper following agarose gel electrophoresis, and hybridizing with two subcloned fragments internal to the P element. The absence of 0.84 and 1.5 kb bands in host DNA (See FIG. 1A) confirmed that no complete P elements are present in the sn$^w$ M strain. Lines 301-2, 101-2 and 101-4, which were phenotypically stable, did not show the presence of any bands not observed in sn$^w$ host DNA. However, DNA from the unstable lines 301-1, 301-3, and 101-3 showed strong bands of hybridization at 0.84 kb and 1.5 kb (see FIG. 1A), consistent with the presence of one or several complete P factors. This correlation between continued mutability and the presence of new P element sequences was verified by similar experiments on the progeny of 8 other injected embryos.

If the integration of P element sequences in the mutable lines occured by a true transposition mechanism, then they should contain the entire P element sequence located between the target DNA sequences, but lack the flanking Drosophila and pBR322 vector sequences in p$\pi$25.1. These expectations were verified by additional gel transfer experiments.

Probes specific for vector sequences, flanking chromosomal sequences (isolated from a strain lacking a P factor at this site) or the P factor itself were used. Each of five independent mutable strains was shown to contain a complete, intact P factor, but to lack any new sequences complementary to flanking Drosophila DNA in p$\pi$25.1 or to pBR322 DNA. These results show that the P factor or p$\pi$25.1 DNA transposed into the chromosomes as a discrete entity as expected for a specifically catalyzed event.

To determine if the P factors which had transposed into the genomes of the line 301-1, and numerous other independently derived mutable strains were inherited, additional generations of flies from these strains were examined. Hypermutability of the singed gene was observed in all cases, indicating that the P factors were stably inherited following transfer into recipient chromosomes.

EXAMPLE 2

Correction of a Genetically Determined Deficiency for the Enzyme Xanthine Dehydrogenase in Drosophila by Introduction of a Transposon Containing a Functional Gene Encoding Xanthine Dehydrogenase Drosophila homozygous for mutant alleles of the rosy (ry) gene (such as ry$^{60}$ or ry$^{42}$) lack detectable activity of the enzyme xanthine dehydrogenase (XDH).

As a result they have abnormal rosy-colored eye pigmentation and are unable to detoxify compounds such as purine. And 8.1 Kb Sal I fragment of Drosophila DNA believed to contain the wild-type XDH gene was cloned in pBR322, giving rise to the plasmid pDM2844S8.5 (see FIG. 1B). This example demonstrates that by using the method of this invention: (1) a plasmid (pry1) containing a transposon (ry1) carrying the rosy+ gene can be constructed; (2) the plasmid DNA can be introduced into germline cells of rosy mutant embryos; and (3) the ry1 transposable element on pry1 can be caused to affirmatively insert into the genome of the rosy mutant germline cells in such a manner as to result in a full and permanently heritable correction of the eye color defect associated with the rosy mutation in the progeny derived from these germline cells.

The plasmid pry1 containing the transposon ry1 was constructed as shown in FIG. 4. (Details of methods used in this construction are given in Wu, Ed., supra and Maniatis et al (1982), supra.) Part of pry1 was derived from a plasmid (p6.1, FIG. 1C) which contain a 2.1 kb Sal fragment of Drosophila genomic DNA containing a P element which had undergone deletion of 1.7 kb of the sequences between its termini. This P element was still capable of transposition if transposase was supplied by a second complete P element (Rubin et al., *Cell*, 29, 987 (1982). The remainder of pry1 was derived from pDm2844S8.5 (see FIG. 1B).

Briefly, pDm2844S8.5 was digested with Sal I endonuclease (available from New England Biolabs) and the two fragments which resulted were separated by size using gel electrophoresis. The larger fragment, which contained the ry+ gene (see FIG. 1B) was purified and added to an equal amount of p6.1 DNA cleaved by Xho I (available from Bethesda Research Labs). Xho cuts at p6.1 once at a site between the P factor termini. Furthermore, DNA cut with Xho I and DNA cut with Sal I can be readily ligated together since their ends are complementary. Ligation of the mixture with T4 DNA ligase (available from New England Biolabs) yielded circular DNA molecules which were used to transform *E. coli* HB101. Ampicillin-resistant colonies were selected and the plasmid DNA in 10 colonies was characterized by digestion with restriction enzymes. One of these, pry1 (see FIG. 3) was determined to result from the desired insertion of the 8.1 kb Sal fragment into the Xho site of p6.1. Another plasmid, pry3, was obtained in which the orientation of the 8.1 kb Sal I fragment inserted into the p6.1 Xho I site was the reverse of that in pry1.

p6.1 contained a modified P element that was capable of transposition in response to transposase. Since the Xho I site was located within this transposon, the insertion of the 8.1 kb Sal I fragment containing the ry+ gene at this site resulted in the creation of a new transposon as well as a new plasmid. This transposon was designated ry1. It was defined by the same target sequences as in the parent plasmid but includes 8.1 kb of additional DNA sequence. In the presence of transposase, the entire ry1 transposon carrying the ry+ gene would now be expected to transpose.

The plasmids pry1 and pry3 were introduced into germline cells of Drosophila embryos homozygous for ry$^{60}$ or ry$^{42}$ using the same technique of microinjection described in Example 1. To cause the rosy+ transposon to be affirmatively inserted into such germline cells, a plasmid (pπ25.1, see FIG. 1A) containing a complete P element capable of providing transposase was also injected along with pry1 and pry3. Two basic protocols for providing such complementing transposase activity are illustrated in FIG. 4. In the first protocol (FIG. 4, Method 1), plasmids containing the rosy transposon were injected into dysgenic embryos derived from a cross between rosy homozygous mutant flies. P elements are known to transpose at high rates in the developing germline of such dysgenic embryos and high levels of transposase activity would be expected to be present.

In the second protocol (FIG. 4, Method 2), a mixture of plasmid DNAs containing the rosy transposon and the 3 kb P element was co-injected into embryos lacking P elements. As shown in Example 1, the 3 kb P element, when injected into such an embryo, produced sufficient transposase acitivty to catalyze its own transposition from the injected plasmid DNA into chromosomal sites. The transposase produced by the 3 kb P element might similarly act on the rosy transposon ry1 to also cause its transposition into the genome when both DNAs were co-injected. In these experiments plasmid DNAs containing rosy transposon and the 3 kb element DNA were injected in a 6:1 or 20:1 ratio (wt/wt) to favor transfer of the ry1 transposon. All injected embryos were homozygous for mutations at rosy to permit phenotypic screening for successful gene transfer events.

Table 5 summarizes the results using each of the above protocols. Both protocols resulted in successful transfer of a functional rosy gene or genes as assayed by production, among the G1 progeny of the injected embryos, of adult flies with wild-type eye color. In the case of those injected embryos that gave ry+ progeny, the percentage of their G1 progeny that were rosy+ varied between 0.4 and 39 as shown in Table 6. In the G2 generation the ry+ phenotype was inherited in a manner expected for a stable dominant marker.

To confirm that the inheritance of the ry+ eye color phenotype was due to the chromosomal integration of the rosy transposon, DNA from ry+ and ry- segregants of the three ry+ lines generated in Run Nos. 1 and 2 were analyzed. DNA was prepared from the host strain, which was homozygous for the rosy mutant allele ry$^{60}$, and separately from ry+ and ry- G2 progeny of each of the three lines. These DNAs were digested with Sal I, an enzyme that does not cut within the rosy transposon sequences (see FIG. 1D). The resultant digests were then factionated by gel electrophoresis, transferred to nitrocellulose paper and hybridized with pDm2844S8.5, a plasmid carrying the cloned 8.1 kb Sal I fragment containing the ry+ gene. The band of hybridization corresponding to the ry$^{60}$ mutant allele, which contains a 0.9 kb deletion relative to wild type, was seen in all DNA samples. In each line, DNA from the ry+ G2 flies had one or two additional bands of hybridization. Lines R102 and R113 (see Table 6) each had one additional band of >25 kb and 14 kb respectively, while line R202 (see Table 6) had two additional bands of 24 and 16 kb. DNA from the ry- flies of these lines did not contain additional bands. Thus the additional genomic copies of rosy DNA segregated with the ry+ eye color phenotype in each case indicating that these additional rosy DNA sequences were responsible for the ry+ eye color.

Some of the adult flies which developed from the injected rosy mutant embryos (i.e., G0 adults) themselves showed wild type or nearly wild type eye color. In experiments 3, 4 and 5 of Table 5, 17 of 40 fertile G0 adults (42%) had a ry+ eye color phenotype. Of the 21

G0 adults which produced ry+ G1 progeny (Table 6) 8 had the wild type eye color. These observations suggest that transposable element mediated gene transfer can be used to alter characteristics of the DNA recipient (G0 generation) as well as those of its G1 progeny.

Studies on the transposition of the 3 kb P element from injected plasmid DNA, (as in Example 1), showed that only the P element sequences, and not the remainder of the plasmid, were inserted into the genome of the recipient. Additional gel transfer experiments verified that a similar integration mechanism operates in the case of injected plasmids containing the rosy transposon. Thus only the ry1 transposon sequences could be detected in the recipient genome; other sequences from pry1 were not detected.

To determine the chromosomal sites at which ry1 integration had occurred, chromosomes were prepared from G2 larvae and subjected to in situ hybridization as in Example 1. Each of the nine ry+ lines tested had one or two new chromosomal sites complementary to ry1.

TABLE 5
SUMMARY OF ROSY GENE TRANSFER EXPERIMENTS

| Run Number | DNAs Injected[1] | Host Embryos[2] | Number Injected | Number of Fertile Adults | Number Giving Progeny ry+ |
|---|---|---|---|---|---|
| 1 | pry$^1$ + pry$^3$ | M/P* ry$^{60}$ | 147 | 9 | 2 (22%)[3] |
| 2 | pry$^1$ + pry$^3$ pπ25.1 | M ry$^{60}$ | 114 | 5 | 1 (20%) |
| 3 | pry$^1$ + pry$^3$ pπ25.1 | M ry$^{42}$ | 215 | 19 | 11 (58%) |
| 4 | pry$^1$ + pry$^3$ pπ25.7 | M ry$^{42}$ | 121 | 17 | 5 (29%) |
| 5 | pry$^1$ pπ25.7 | M ry$^{42}$ | 87 | 4 | 2 (50%) |
| 6 | pry$^1$ + pry$^3$ pπ25.7Δ | M ry$^{42}$ | 427 | 28 | 0 (0%) |

*M/P indicates an embryo with a P father and M mother.
[1]DNAs were injected in 5 mM KCl, 0.1 mM sodium phosphate pH 6.8 at the following concentrations. Run No. 1: pry$^1$ and pry$^3$ each at 500 μg/ml. Run No. 2: pry$^1$ and pry$^3$ each at 500 μg/ml; pπ25.1 at 50 μg/ml. Run No. 3: pry$^1$ and pry$^3$ each at 150 μg/ml; pπ25.1 at 50 μg/ml. Run No. 4: same as Run No. 3 except pπ25.7 was substituted for pπ25.1. pπ25.1 is identical to pπ25.1 except the orientation of the Drosophila DNA insert relative to the pBR322 vector is reversed. Run No. 5: pry$^1$ at 300 μg/ml; pπ25.7 at 50 μg/ml. Run No. 6: pry$^1$ and pry$^3$ each at 150 μg/ml; pπ25.7Δ at 50 μg/ml. pπ25.7Δ plasmids were constructed by deleting various portions of the 3 kb P element carried on pπ25.7. The data from four different deletions have been pooled.
[2]The cytotype and genotype of the injected embryos are shown.
[3]The percentages indicate the fraction of fertile adults that gave ry+ individuals among their progeny.

The ability to control transposition by limiting the availability of transposase was illustrated in the experiments of Run No. 6 of Table 5. When sequences within the 3 kb P element cloned in pπ25.7 were partially deleted, the resulting plasmids could no longer code for the production of active transposase. No transposition events were observed when they were substituted for the complete P element in these experiments. Thus, transposition can be controlled by controlling the availability of the DNA sequences which encode transposase. It could also be controlled by modifying the P element sequences in pπ25.7 so that transposase protein was produced in only the cell types of interest.

The ry+ transposons which had integrated into the chromosomes of the ry− recipient functioned at a sufficient level to correct their eye color defect. The level of function and developmental regulation of the rosy genes contained with transposons that had inserted into host chromosomes at a variety of chromosomal sites were also studied directly.

Eighteen strains each containing a single ry+ transposon at a different chromosomal site were studied. These transposons had the structure show in FIG. 1D for ry1 and were transferred into the chromosomes by the experimental protocol of FIG. 4, Method 2. The activity of the enzyme encoded by the rosy gene xanthine dehydrogenase, was measured in extracts of adults from the 18 strains, and compared to the ativity of wild-type adults. In all 18 cases, the XDH levels were similar to those seen in the wild-type strain, indicating that the rosy gene present in the transposon functioned at a level similar to that of a rosy gene in its normal surroundings on Drosophila chromosome 3. The mean XDH activity of a wild-type XDH gene was 0.46±0.02 (arbitrary units) in these experiments, while the mean activity of the exogenous genes was 0.44±0.27.

To determine if the rosy genes were expressed in the appropriate tissues, histochemical staining for XDH activity was carried out (as described in A.T.C. Carpenter, *Proc. Nat. Acad. Sci.* (USA) 79:5961 (1982)). All of the 18 lines showed evidence of activity in adult Malphigan tubes and larval fat body cells, but little or no activity was observed in the adult testis. Strains carrying wild type rosy genes at the normal locus showed the same pattern of XDH activity in these experiments. Thus rosy genes transferred into host chromosomes by the method of the present invention, came under the normal developmental controls recognized by this gene during the Drosophila life cycle.

The inheritance of the transferred rosy genes was studied by crossing individual males from each of the 18 lines to rosy mutant females and determining the rosy phenotype of the progeny. The rosy transposon was inherited in a normal Mendelian manner in all 18 strains for as many generations as testing has continued. Transposition of the rosy gene containing transposon could be reinitiated, however, by introducing a complete P element(s) into the strain through a genetic cross to a strain carrying such a complete element(s). This further illustrates how transposition can be controlled by controlling the presence of complete P elements which can produce transposase.

TABLE 6
SUMMARY OF THE PHENOTYPES OF G0 AND G1 INDIVIDUALS

| G0 Fly Number | G0 rosy Expression* | G1 Progeny rosy− | G1 Progeny rosy+ |
|---|---|---|---|
| R102 | − | 158 | 6 |
| R113 | − | 173 | 6 |
| R202 | − | 51 | 32 |
| R301 | + | 237 | 2 |
| R302 | + | 243 | 14 |
| R303 | + | 133 | 5 |
| R304 | − | 134 | 11 |
| R305 | − | 234 | 1 |
| R306 | + | 39 | 2 |
| R307 | − | 249 | 2 |
| R308 | − | 214 | 4 |
| R309 | − | 152 | 2 |
| R310 | − | 149 | 1 |
| R311 | − | 119 | 3 |
| R401 | + | 113 | 15 |
| R402 | + | 154 | 27 |
| R403 | − | 142 | 5 |
| R404 | + | 241 | 6 |
| R405 | − | 84 | 7 |
| R501 | − | 96 | 1 |
| R502 | + | 52 | 16 |

*The eye color phenotypes of G0 adults was scored either − (unchanged from the rosy eye color of the host ry$^{60}$ or ry$^{42}$ strain) or + (wild-type eye color either partially or completely restored).

EXAMPLE 3

Insertion of an Unselected DNA Segment Encoding Two Eggshell Proteins into the Drosophila Genome Frequently, transfer of DNA sequences that do not confer on the recipient cells or organism an easily recognizable phenotype (hereinafter "unselected DNA sequences") may be desired. For example, the insertion of a storage protein gene into a plant protoplast cell or of a globin gene into an erythropoetic stem cell would not usually be expected to result in an immediate easily detected phenotypic change. To demonstrate that the method of this invention provides the ability to transfer such unselected DNA sequences, DNA sequences encoding two Drosophila melanogaster eggshell proteins (Spradling, Cell, 27, 193 (1981)) were inserted into the germ line of $sn^w$ M embryos.

An eggshell gene transposon was constructed using a cloned DNA p302.77 (Spradling, Cell, 27, 193 (1981)) which contains 3 eggshell protein genes. p302.77 plasmid DNA was cut with Sal I and the 3.7 kb fragment was isolated after electrophoresis on an agarose gel. The purified Sal I fragment was ligated to p6.1 DNA which had been cut with XhoI. The construction of this transposon was therefore analogous to that of pry1, except that three copies of the 3.7 kb Sal I fragment from p302.77 were inserted instead of a single 8.1 kb Sal I fragment from pDm2844S8.5 (see Example 2). This plasmid was designated pch1, as shown in FIG. 1E, and contains a new transposon ch1 containing the inserted sequences from p302.77. FIG. 5 describes the protocol used to insert ch1 into the chromosomes of $sn^w$ embryos. pch1 plasmid DNA (1 mg/ml) was mixed with p$\pi$25.1 DNA (50 $\mu$g/ml) and injected into $sn^w$ M embryos as described in Example 1. Individual adult flies developing from the injected embryos were mated to y $sn^w$ males or attached-X females (see FIG. 5 legend) and the G1 progeny males were evaluated for the presence of the singed phenotype. G1 progeny males with wild type or singed extreme bristles indicated that the injected p$\pi$25.1 DNA had been expressed in at least some of the germline cells of the corresponding parental germline. The presence of levels of p$\pi$25.1-encoded proteins sufficient to catalyze $sn^w$ mutations would also catalyze at high frequency the insertion into the genome of the eggshell gene transposon ch1. Therefore, lines were established from individual males which had undergone singed phenotype changes and from their singed weak brothers (G1 lines).

The presence of the eggshell gene transposon in these lines was investigated by gel transfer hydridization using DNA from adult flies and by in situ hydridization to larval salivary gland chromosomes, using the 3.7 kb Sal I fragment from p302.77 as a probe. One line was found which contained inserts of the eggshell gene transposon located at four different sites on its chromosomes. These inserted eggshell genes were inherited in a stable manner. Table 7 below summarizes the results obtained.

TABLE 7

Transfer of Unselected DNA Sequences Encoding Two Eggshell Proteins into y $sn^w$ Drosophila Embryos

| Number Injected | Number Producing Mosaic Progeny | Number With Eggshell Transposons in Genome |
|---|---|---|
| 25 | 3 | 1 (33%) |

Note: Not all progeny of the mutable flies were tested, hence 33% is a minimal figure.

Since no property of the eggshell gene transposon was used in these experiments other than its ability to hybridize specifically to a complementary nucleic acid probe, any nucleic acid sequence not directly deleterious to the recipient could be inserted into the Drosophila genome in an analogous manner using the process of this invention.

Many other genetic markers could be used in place of the singed weak gene to allow detection of unselected sequences. Genes conferring a visible property such as the rosy gene or dominant selectable markers such as antibiotic resistance genes (as described in Colbere-Garapin et al., J. Mol. Biol., 150, 1 (1980)) could also be used. Transposons carrying these genes could be injected along with transposons carrying the unselected sequences. Some progeny in which the selected transposon had inserted would also probably contain one or more copies of the unselected transposon. The frequency of such co-transfer has been increased further by constructing single transposons containing both the selected and unselected DNA sequences.

From the above examples, it can be seen that the method of this invention provides the ability to insert desired DNA fragments into the cells of multi-cellular organisms where the characteristics of this DNA are faithfully expressed and heritably transmitted to organism progeny. Where the exogenous DNA sequence contains a gene for which the organism is deficient, genetic deficiency correction is thereby possible using the method of this invention.

While the invention has been described in detail and with respect to various embodiments thereof, it is apparent that various changes and modifications may be made therein without departing from the spirit and scope thereof.

What is claimed is:

1. A method for incorporating a desired foreign exogenous DNA sequence into the genome of a Drosophila insect comprising:
   (1) producing a transposable element of DNA, wherein said transposable element is derived from the P element isolated from Drosophila melanogaster and comprises a defined sequence of nucleotide base pairs, wherein the defined sequence of nucleotide base pairs comprises at least two sets of target sequences recognized by transposase and a fragment of foreign exogenous DNA located between said sets of target DNA sequences, wherein said fragment of foreign exogenous DNA encodes for a structural gene, a regulatory gene or other functional DNA;
   (2) incorporating the transposable element used in (1) above in a germ cell of a Drosophila insect; and
   (3) causing the transposable element to be affirmatively inserted into the genome of the recipient Drosophila insect so as to become part of the heritable genome of the Drosophila insect, wherein said Drosophila insect is one in which said transposable element can function to affirmatively insert said foreign exogenous DNA into the genome thereof.

2. The method of claim 1, wherein said foreign exogenous DNA comprises a nucleotide base pair sequence encoding for a foreign protein.

3. The method of claim 2, wherein said foreign protein is an enzyme.

4. The method of claim 1, wherein said foreign exogenous DNA comprises a nucleotide base pair sequence encoding for a protein recognition site, a binding site or a cleavage site.

5. The method of claim 1, wherein said foreign exogenous DNA comprises a nucleotide base pair sequence encoding for an origin of DNA replication.

6. The method of claim 1, wherein said foreign exogenous DNA comprises a nucleotide base pair sequence encoding for an enhancer sequence.

7. The method of claim 1, wherein said foreign exogenous DNA comprises a nucleotide base pair sequence encoding for an RNA.

8. The method of claim 1, wherein said foreign exogenous DNA comprises a nucleotide base pair sequence encoding a gene causing dominant sterility in a target species.

9. The method of claim 8, wherein said target species is an insect.

10. The method of claim 1, wherein said foreign exogenous DNA comprises a nucleotide base pair sequence encoding for *Drosophila melanogaster* $B2t^D$ gene.

* * * * *